United States Patent [19]

Jansen et al.

[11] Patent Number: 4,595,015
[45] Date of Patent: Jun. 17, 1986

[54] METHOD AND APPARATUS FOR ESTIMATING THE CARDIAC OUTPUT OF THE HEART OF A PATIENT

[75] Inventors: Jozef R. Jansen, Noordwijkerhout; Adriaan Versprille, Rotterdam, both of Netherlands

[73] Assignee: Erasmus Universiteit Rotterdam, Netherlands

[21] Appl. No.: 527,419

[22] Filed: Aug. 29, 1983

[30] Foreign Application Priority Data

Apr. 18, 1983 [NL] Netherlands ............. 8301279

[51] Int. Cl.$^4$ .................................. A61B 5/02
[52] U.S. Cl. .................................. 128/713; 128/692
[58] Field of Search ............ 128/713, 691–692, 128/670–671, 668; 13/204

[56] References Cited

U.S. PATENT DOCUMENTS

| | | | |
|---|---|---|---|
| 3,304,413 | 2/1967 | Lehmann et al. | 128/713 X |
| 3,433,935 | 3/1969 | Sherman | 128/691 X |
| 3,651,318 | 3/1972 | Czekajewski | 128/691 X |
| 3,987,788 | 10/1976 | Emil | 128/713 |
| 4,035,622 | 7/1977 | Obermajer | 128/713 |
| 4,120,295 | 10/1978 | Hill | 128/692 |
| 4,326,539 | 4/1982 | Obermajer | 128/713 |

OTHER PUBLICATIONS

Wilson; "Applic. of Thermal-Electronic Instrumentation to Biol. Flows"; Proc. of 8th Ann. 1969 IEEE Region III Conv., 11-1969, pp. 45–50.

Primary Examiner—Kyle L. Howell
Assistant Examiner—Angela P. Sykes
Attorney, Agent, or Firm—Kane, Dalsimer, Kane, Sullivan and Kurucz

[57] ABSTRACT

A method and apparatus are described for estimating the cardiac output of the heart of a patient. An indicator is injected as an impulse in the blood stream of the patient, whereafter a first signal corresponding with the concentration variation of the indicator is measured at a position at a distance downstream of the injection position. Said first signal is supplied to a processor unit for determining the cardiac output from said first signal and the injected amount of indicator. Further, a second signal at least substantially proportional to the cardiac output is measured in the same blood stream adjacent the measurement position for the first signal. Both said signals are stored in a memory. Thereafter, said second signal is normalized by a predetermined value of said second signal and the first signal is corrected by means of the normalized second signal. The processor unit now determines the cardiac output from the corrected first signal.

9 Claims, 2 Drawing Figures

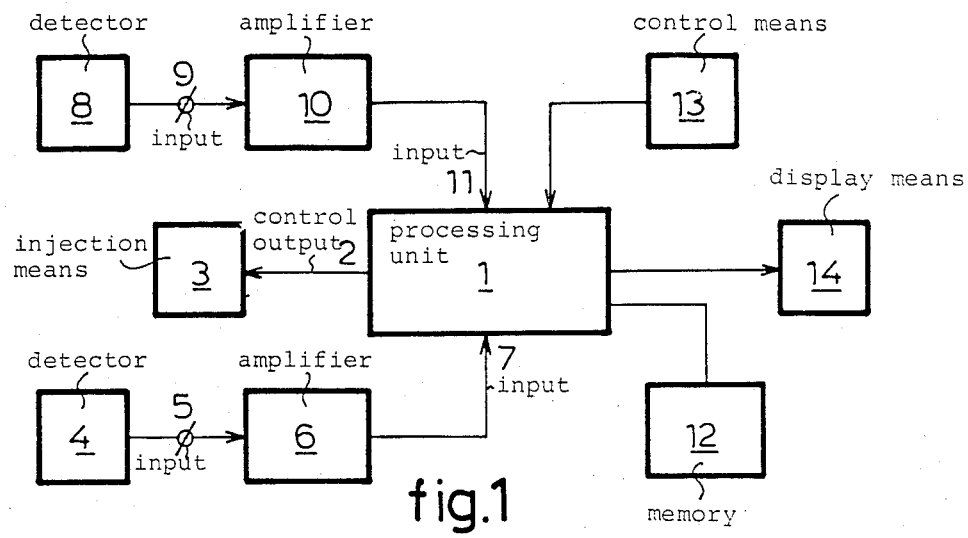
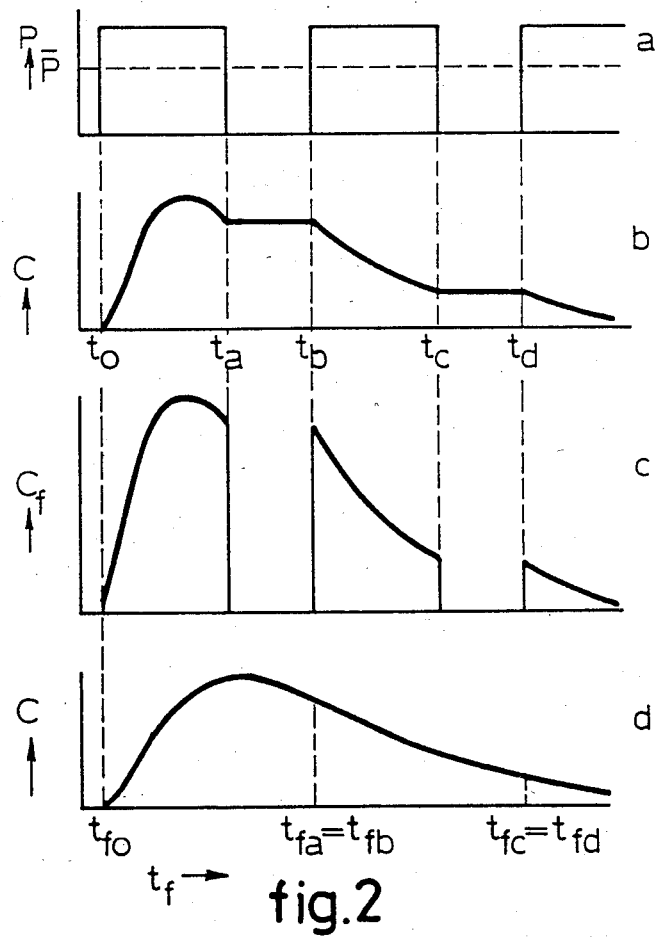

METHOD AND APPARATUS FOR ESTIMATING THE CARDIAC OUTPUT OF THE HEART OF A PATIENT

BACKGROUND OF THE INVENTION

The invention relates to a method and an apparatus for estimating the cardiac output of the heart of a patient, wherein an indicator is injected as an impulse in the blood stream of the patient, and a first signal corresponding with the concentration variation of the indicator is measured at a position at a distance downstream of the injection position, said first signal being supplied to a processor unit for determining the cardiac output from said first signal and the injected amount of indicator.

According to a known method of this kind, which normally is referred to as dilution method, a catheter is placed in the blood stream of the patient by means of which the indicator, for example a relatively cold fluid, salt, a colorant or the like, is injected in the blood, wherein said catheter comprises a detector downstream of the injection position for measuring the concentration of the injected indicator. In this manner a so-called dilution curve can be estimated which indicates the course of the indicator concentration. As the injected amount of indicator is known, the cardiac output can be determined from this information. In this case it is a precondition that the cardiac output is constant. In practice it is proved that the cardiac output pulsating due to the heart action can be considered as constant. However, when the patient is ventilated by a ventilation apparatus, the cardiac output is affected in such a manner that it can not be considered as a constant, but on the contrary shows a fluctuating character, whereas under these circumstances an accurate determination of the cardiac output is desired because the cardiac output is one of the criteria for determining the condition of the patient. Experiments have shown that at the determination of the cardiac output by means of this known method, the measuring results can show a spread of 65-125% of the average value.

According to an other known method, normally referred to as pulse contour method, a catheter is placed in the blood stream of the patient, by means of which a signal is measured, which signal is substantially proportional to the cardiac output. For the estimation of the cardiac output it is assumed that the characteristic impedance of the vascular system downstream of the measuring place is constant. However, this condition is not fulfilled in practice because said characteristic impedance is varying with a relatively large time constant. Thereby, reliable measuring results cannot be obtained by this known method.

OBJECTIVES AND SUMMARY OF THE INVENTION

The invention aims to provide a method of the above-mentioned kind, wherein said disadvantages are obviated in a simple but nevertheless effective manner.

To this end, a second signal at least substantially proportional to the cardiac output is measured in the same blood stream adjacent the measurement position for the first signal, and both signals are stored in a memory, whereafter said second signal is normalized by a predetermined value of said second signal and the first signal is corrected by means of the normalized second signal, wherein the processor unit determines the cardiac output from the corrected first signal.

In this manner the influence of the varying cardiac output on the first signal is substantially completely eliminated so that the cardiac output can be determined with high accuracy. Experiments have shown that the estimation of the cardiac output by means of the method according to the invention shows an accuracy of 5-10%.

According to the invention said first signal can be multiplied by said normalized second signal.

Preferably, the time axis of said first signal is transformed by means of said normalized second signal. Thereby, the dilution curve determined by the first signal can be approximated very accurately by model functions, whereby computations of the leakage and/or recirculation portion in the dilution curve can be done with a high accuracy.

According to the invention said second signal can be normalized by a value of said second signal for one stroke volume of the heart, wherein the proportionality constant between said second signal and the cardiac output is determined by means of the cardiac output determined by the processor unit and said value of the second signal for one stroke volume of the heart, whereafter said processor unit continuously determines the cardiac output from said second signal. Thereby, it is possible to continuously follow the time course of the average cardiac output per heart-beat as long as the circumstances do not vary, i.e. as long as the proportionality constant does not vary.

The invention further relates to an apparatus for estimating the cardiac output of the heart of a patient by means of the above-mentioned method, said apparatus comprising a processor unit having a first input for a first signal depending on the concentration of an indicator in the blood stream of a patient, a control output for controlling an injection means for injecting an indicator in the blood stream of the patient, and a computing means for determining the cardiac output from said first signal and the injected amount of indicator, wherein said processor unit comprises a second input for a second signal at least substantially proportional to the cardiac output, and a memory for storing both said signals, wherein said computing means normalizes said second signal by a predetermined value of said second signal and corrects the first signal by means of the normalized second signals, while the computing means determines the cardiac output from the corrected first signal.

The invention will hereinafter be further explained by reference to the drawings, in which an embodiment is shown.

BRIEF DESCRIPTION OF THE DRAWINGS

FIG. 1 shows a simplified block diagram of an embodiment of the apparatus according to the invention.

FIG. 2 schematically shows some diagrams for the explanation of the method according to the invention.

DETAILED DESCRIPTION OF THE INVENTION

Referring to FIG. 1, there is shown a simplified block diagram of an apparatus for estimating the cardiac output of the heart of a patient. The apparatus comprises a processing unit 1 with a control output 2, by means of which the processor unit 1 can control a schematically shown injection means 3 for injecting an indicator in the blood stream of the patient. To this end, a Swan-Ganz catheter is placed in the blood stream of a patient in a normal way, by means of which the indicator is injected. The indicator is for example a cold fluid, salt, a colorant or the like. Downstream of the injection opening the catheter has a schematically indicated detector 4 for measuring the concentration of the indicator in the blood. This detector 4 is connected to an input 5 of the apparatus described. The measuring signal obtained is amplified by an amplifier 6 and supplied to a first input 7 of the processor unit 1.

In this manner a so-called dilution curve showing the time course of the concentration can be estimated, from which the cardiac output can be computed as the injected amount of indicator is known. For, the following equation applies $$m_i = \int C(t) \cdot Q(t) \, dt \tag{1}$$

in which $m_i$ is the injected amount of indicator, $C(t)$ is the course of the concentration and $Q(t)$ is the cardiac output. From this it follows that $$\dot{Q}(t) = \frac{m_i}{\int C(t)\,dt}.$$

Examinations have shown that accurate measuring results cannot be obtained in this manner because the pulsating cardiac output has a fluctuating character, in particular when the patient is ventilated by a ventilation apparatus.

In order to eliminate the influence of a varying cardiac output, a second signal is measured which is substantially proportional to the cardiac output. To this end, the pressure adjacent the detector 4 is measured by means of a schematically shown detector 8 accommodated in the same catheter. However, it is possible also to measure the flow of the blood adjacent the detector 4. Said second signal is supplied to an input 9 of the apparatus and after being amplified by an amplifier 10 to a second input 11 of the processor unit 1. During a measurement of the course of the concentration, the processor unit 1 stores both said signals in a memory 12. For the estimation of the average cardiac output said second signal is normalized by the average of said second signal over a respiration. For, from the above-mentioned equation (1) it follows that $$m_i = \bar{Q} \int C(t) \cdot \frac{\dot{Q}(t)}{\bar{Q}} \, dt$$

from which it follows for the average cardiac output $$\bar{Q} = \frac{m_i}{\int C(t) \cdot \frac{\dot{Q}(t)}{\bar{Q}} \, dt}$$

This equation shows that said first signal can be corrected with the normalized second signal whereby a reliable estimation of the average cardiac output is obtained.

Referring to FIG. 2 there are shown some schematical diagrams for further explanation. FIG. 2(a) shows a theoretical pressure course, while FIG. 2(b) shows a corresponding dilution curve. From FIG. 2(b) it appears that the dilution curve is indeed strongly influenced by a varying cardiac output. FIG. 2(c) shows the corrected dilution curve which is obtained by multiplying the measured concentration course by the normalized second signal in accordance with the equation $$C_f = C(t) \cdot \frac{\dot{Q}(t)}{\bar{Q}}$$

As an alternative for the correction according to FIG. 2(c), the concentration course can be corrected according to the equation $$t_{fn} = t_{n-1} + \frac{\dot{Q}(t)}{\bar{Q}} \cdot (t_n - t_{n-1}).$$

Thereby, the time axis of the concentration course is corrected which has the advantage that the corrected dilution curve now corresponds to an expected dilution curve, whereby an accurate approximation is possible by means of usual model functions. The manner for correction of said first signal by means of the normalized second signal can be selected by a control means 13.

As an alternative said second signal can be normalized by a value of said second signal for one stroke volume of the heart. The value by which the second signal is normalized, can be selected also by said control means 13. In this case, the proportionality factor between said second signal and the cardiac output can be computed from the estimated cardiac output. The processor unit 1 is now able to continuously follow the average cardiac output per heart-beat in time as long as the circumstances remain such that the computed proportionality factor holds. When this condition is no longer fulfilled, an indicator can be injected again in the blood stream of the patient and the measurement for estimating the cardiac output can be repeated in the above-described manner.

It is noted that all measuring results can be displayed by a suitable display means 14.

The invention is not restricted to the above-described embodiment which can be varied in a number of ways within the scope of the invention.

We claim:

1. A method for estimating the cardiac output of the heart of a patent comprising the steps of:
    injecting an indicator as an impulse at a first position in the blood stream of the patent;
    measuring a first signal corresponding to the concentration variation of the indicator at a second position at a distance downstream of said first position, said first signal being supplied to a processor unit;
    measuring a second signal at least substantially proportional to the cardiac output, adjacent said first position;
    storing said first and second signals in a memory;
    normalizing said second signal by a predetermined value to obtain a normalized second signal;
    correcting said first signal by said normalized second signal to obtain a corrected signal; and
    determining the cardiac output from said corrected signal by said processor unit.

2. Method of claim 1, wherein said first signal is multiplied by said normalized second signal.

3. Method of claim 1, wherein the time axis with respect to concentration variation of said first signal is transformed by means of said normalized second signal.

4. Method of claims 2 or 3, wherein said second signal is normalized by the average of said second signal over one respiration cycle.

5. Method of claims 2 or 3, wherein said second signal is normalized by a value of said second signal for one stroke volume of the heart.

6. Method of claim 5, wherein the proportionality constant between said second signal and the cardiac output is determined by means of the cardiac output determined by the processor unit and said value of the second signal for one stroke volume of the heart, whereafter said processor unit continuously determines the cardiac output from said second signal.

7. Apparatus for estimating the cardiac output of the heart of a patient, comprising an injection means for injecting an indicator in the blood stream of the patient a processor unit having a first input for a first signal dependent on the concentration of the indicator in the blood stream of a patient, a control output means for controlling said injection means and a computing means for determining the cardiac output from said first signal and the injected amount of indicator, wherein said processor unit comprises a second input for a second signal at least substantially proportional to the cardiac output, and a memory means for storing both said signals, wherein said computing means normalizes said second signal by a predetermined value of said second signal and corrects the first signal by means of the normalized second signal, while the computing means determines the cardiac output from the corrected first signal.

8. Apparatus of claim 7, wherein a control means is provided for selecting the value by which the second signal is normalized.

9. Apparatus of claim 8, further comprising means for determining the proportionality constant between the second signal and the cardiac output of the heart from the cardiac output as determined by the computing means.

* * * * *